United States Patent [19]
Atkinson et al.

[11] Patent Number: 5,105,650
[45] Date of Patent: Apr. 21, 1992

[54] MONITORING COMPACTION OF BACKFILL

[75] Inventors: Dick T. Atkinson, Nashua, N.H.; James E. Aplin, Needham, Mass.; Arnis Mangolds, Stow, Mass.; Daniel J. Foley, N. Chelmsford, Mass.

[73] Assignee: Gas Research Institute, Chicago, Ill.

[21] Appl. No.: 490,751

[22] Filed: Mar. 8, 1990

[51] Int. Cl.$^5$ ............... G01N 33/24; G01N 29/18; G01V 1/30

[52] U.S. Cl. ............... 73/12; 73/784; 73/594; 73/597

[58] Field of Search ............... 73/84, 784, 866, 12, 73/594, 597

[56] References Cited

U.S. PATENT DOCUMENTS

| | | | |
|---|---|---|---|
| Re. 31,195 | 4/1983 | Thurner | 73/573 |
| 2,284,707 | 6/1942 | Wilson . | |
| 2,336,500 | 12/1943 | Ostergerg . | |
| 2,624,251 | 1/1953 | Porter . | |
| 3,286,514 | 11/1966 | Anderson . | |
| 3,372,577 | 3/1968 | Bates et al. . | |
| 3,456,496 | 7/1969 | Heller . | |
| 3,492,859 | 2/1970 | Dodge . | |
| 3,529,468 | 9/1970 | Carlson . | |
| 3,537,541 | 11/1970 | Desai et al. | 73/597 |
| 3,641,811 | 2/1972 | Gnaedinger, Jr. et al. | 73/594 |
| 3,998,090 | 12/1976 | Wislocki | 73/12 |
| 4,348,901 | 9/1982 | Vural et al. | 73/84 X |
| 4,398,427 | 8/1983 | Pan | 73/784 |
| 4,495,434 | 1/1985 | Diepers et al. | 310/338 |
| 4,524,625 | 6/1985 | Pabst et al. | 73/84 X |
| 4,543,820 | 10/1985 | Handy et al. | 73/84 |
| 4,614,110 | 9/1986 | Osterberg | 73/84 |
| 4,662,226 | 5/1987 | Wang | 73/784 X |
| 4,802,371 | 2/1989 | Colderara et al. | 73/862.04 |
| 4,856,318 | 8/1989 | Hogan et al. | 73/12 |

FOREIGN PATENT DOCUMENTS

| | | | |
|---|---|---|---|
| 134557 | 6/1987 | Japan | 73/597 |
| 973702 | 11/1982 | U.S.S.R. | 73/784 |
| 1318653 | 6/1987 | U.S.S.R. | 73/594 |

*Primary Examiner*—Tom Noland
*Attorney, Agent, or Firm*—Fish & Richardson

[57] ABSTRACT

Methods and apparatus for monitoring the compaction of backfill material in an excavation include hammer structure for impacting backfill material in the excavation, a sensor module for disposition at the bottom of the excavation to be backfilled that includes a transducer for developing an electric signal in response to energy transmitted through backfill material from the hammer structure, and a control module responsive to electric signals from the sensor module for providing an indication of the quality of compaction of backfill material in the excavation.

17 Claims, 3 Drawing Sheets

MONITORING COMPACTION OF BACKFILL

This invention relates to monitoring systems and more particularly to methods and apparatus for monitoring compaction of backfill for utility excavations and the like.

BACKGROUND OF THE INVENTION

Excavations such as utility trenches, foundations and the like are generally backfilled in layers, termed lifts, with each lift of backfill material be compacted prior to the addition of the next lift. If backfill material is improperly compacted, or if an unsuitable backfill material is used, the backfilled excavation may subside. Subsidance in foundations, roadways or other structures due to improper backfill compaction can necessitate costly and disruptive repairs.

In the proper compaction of backfill in an excavation, each backfill lift should be properly compacted prior to the addition of the next lift; and after all lifts are in place and compacted, the complete backfilled excavation should be proofed to verify that there are no voids, soil bridges, or layers that are not fully compacted. Current monitoring methods such as drop hammer penetration probes, nuclear densitometry and the sand cone method are typically used only to check each lift for proper compaction, and such methods are expensive, time comsuming and cannot be performed in the real time.

SUMMARY OF THE INVENTION

In accordance with one aspect of the invention, there is provided apparatus for monitoring the compaction of backfill material in an excavation that includes hammer structure for impacting backfill material in the excavation, a sensor module for disposition at the bottom of the excavation to be backfilled that includes a transducer for developing an electric signal in response to energy transmitted through backfill material from the hammer structure, and a control module responsive to electric signals from the sensor module for providing an indication of the quality of compaction of backfill material in the excavation.

In preferred embodiments, the sensor module includes a compliant base member of area at least about one-half the area of the base of the excavation to be backfilled. The base member is of electrically-insulating material such as rubber, synthetic rubber, styrofoam or similar polymeric material on which a plurality of piezoelectric transducers are secured in spaced array, together with an overlying protective sheet member, an array of first piezoelectric tranducers disposed along the perimeter of the base member being connected in parallel to a first output conductor and a second piezoelectric transducer generally at the center of the base member being connected to a second output conductor, the output conductors being connected to the control module for transmitting electrical signals to the control module. Proofing apparatus includes a hammer and a third piezoelectric transducer for placement on the top of the backfilled excavation. The control module includes accumulator circuitry for accumulating output signals from the sensor array for providing an indication of the quality of compaction of each lift of backfill material in the excavation, and verifying circuitry responsive to the second and third transducers for providing a transit time (dependent on seismic velocity) indication of impact energy propagation between the third transducer at the top of the backfill material and the second transducer at the bottom of the excavation.

In a particular embodiment, the control module includes peak detection circuitry for sampling electrical signals received from the array of first piezoelectric transducers, circuitry for storing indications of the peak amplitude of signals received during a sequence of compaction intervals, circuitry responsive to the storage circuitry for providing average peak value signals during a pass of the hammer structure such as a compacting tool, comparison circuitry for comparing average peak value signals during a previous compaction pass with average peak value signals during the current compaction pass to provide an indication of the progress of the compaction process; and timing circuitry for providing an indication of impact energy propagation time through backfill material to provide an indication of acceptable compaction after the excavation backfill process has been completed.

In accordance with another aspect of the invention, there is provided a method for monitoring the compaction of backfill in an excavation that includes the steps of placing sensor structure at the bottom of the excavation, adding backfill material to the excavation, compacting the backfill material with a series of compacting impacts, and monitoring the output of the sensor structure as a function of seismic energy from the impacts that impinge on the sensor structure.

Preferably, the method includes the steps of accumulating amplitude signals from the sensor structure and comparing the magnitudes of those amplitudes from successive compacting passes; and after backfill has been completed, verifying the quality of backfill by measuring the propagation time of an energy wave from the top of the backfill material to a sensor at the bottom of the backfill material to provide an indication of the quality of the compaction of the backfill material.

The invention provides effective real-time monitoring of compaction of backfill material in a utility excavation or the like.

BRIEF DESCRIPTION OF THE DRAWINGS

Other features and advantages of the invention will be seen as the following description of a particular embodiment progresses, in conjunction with the drawings, in which.

DESCRIPTION OF PARTICULAR EMBODIMENT

Figure 1:
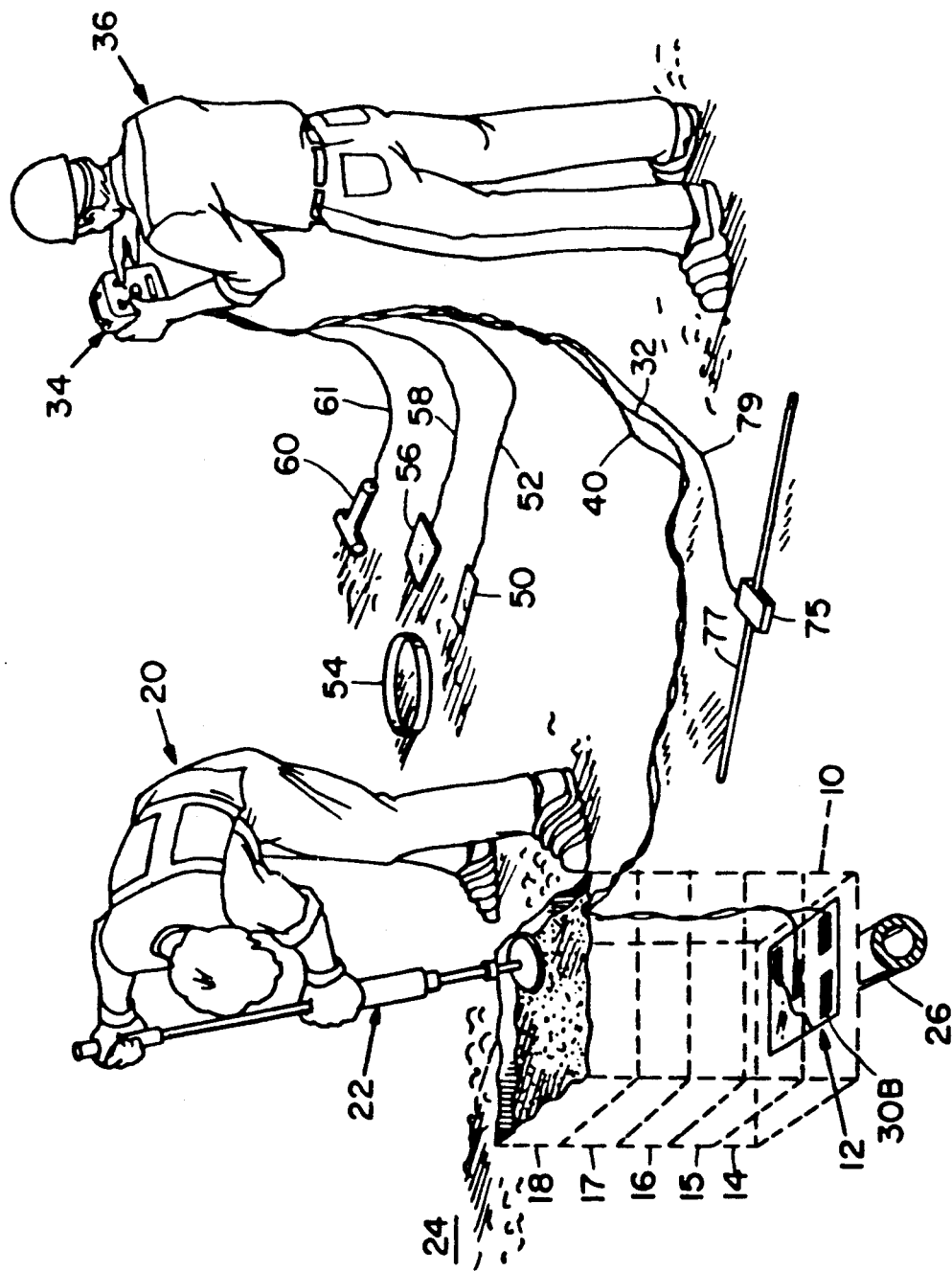
FIG. 1 is a diagrammatic view showing of aspects of a compaction monitoring system in accordance with the invention.

The system diagrammatically shown in FIG. 1 includes excavation 10 in road surface 24 for repair of gas line 26. Gas line 26 has been repaired, sensor module 12 is at the base of excavation 10 and a series of five lifts 14–18 of backfill material are in excavation 10. Operator 20 is using impact tool 22 for compacting the uppermost lift 18. Sensor module 12 has an array of four piezoelectric transducer strips 30A, B, C, D that are connected in parallel by conductors 32 to battery powered portable control module 34 that is operated by observer 36 and a further piezoelectric transducer strip 38 that is connected by conductors 40 to control module 34.

Figure 2:
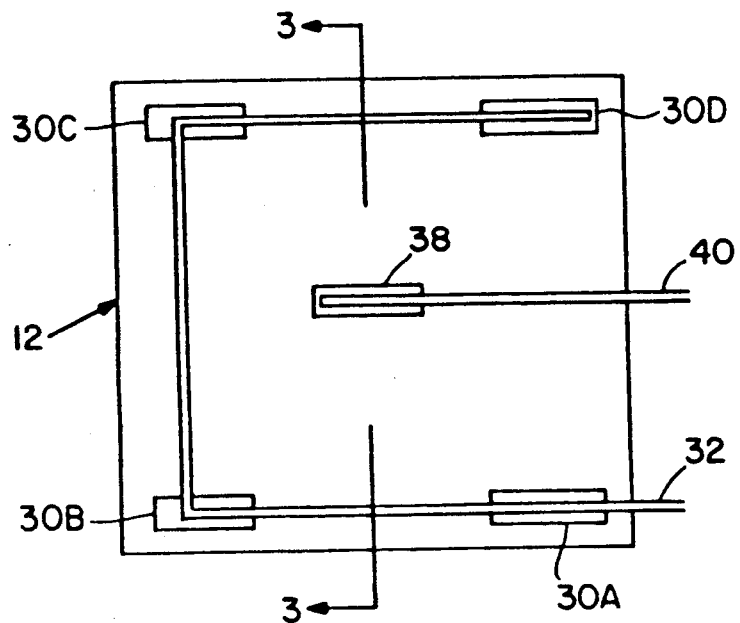
FIG. 2 is a plan view of the sensor module employed in the system of FIG. 1.
Figure 3:
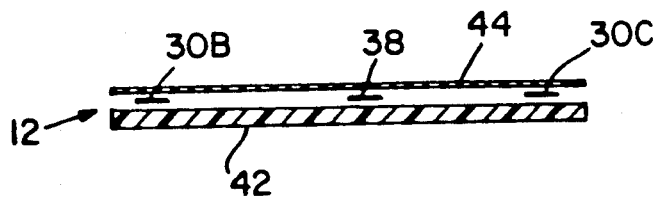
FIG. 3 is a sectional view taken along the line 3—3 of FIG. 2.

Further details of sensor module 12 may be seen with reference to FIGS. 2 and 3. That module includes compliant rubber pad 42 that is about sixty centimeters on a side and has a thickness of about ½ centimeter such that it conforms to the bottom of the excavation 10 and presents the piezoelectric sensors 30, 38 in fixed array. Sensors 30, 38 are of suitable piezoelectric material such as polyvinylidene fluoride (PVDF) film and each film is about two centimeters wide and fifteen centimeters long and metalized for connection to conductors 32, 40. A protective sheet 44 of mylar or similar material overlies and provides protection for sensors 30, 38 and conductors 32, 40 in the excavation 10.

With reference again to FIG. 1, the system also includes PVDF proofing sensor 50 for placement on the surface of the completely backfilled excavation and that is connected to control module 34 by conductor 52, cylindrical spacer 54 (about twenty five centimeters in diameter and five centimeters high) that is adapted to be placed over sensor 50 and filled with backfill material, metal trigger plate 56 that is placed on the surface of the backfill material in spacer 54 and that is connected to control module 34 by conductor 58, and proofing hammer 60 that is connected to control module 34 by conductor 61. The striking of plate 56 by hammer 60 completes a circuit between conductors 58, 61 to activate circuits in microprocessor 84 in anticipation of a timing cycle for proofing the backfilled excavation. The system also includes a sonic transmitter receiver unit 75 that is supported on rod 77 and connected to control module by conductor 79, rod 77 being adapted to be positioned on road surface 24 to bridge hole 10 so that unit 75 is positioned directly above sensor 38 of sensor module 12 for sonic depth measurement before any lift of backfill material is placed in excavation 10.

Figure 4:
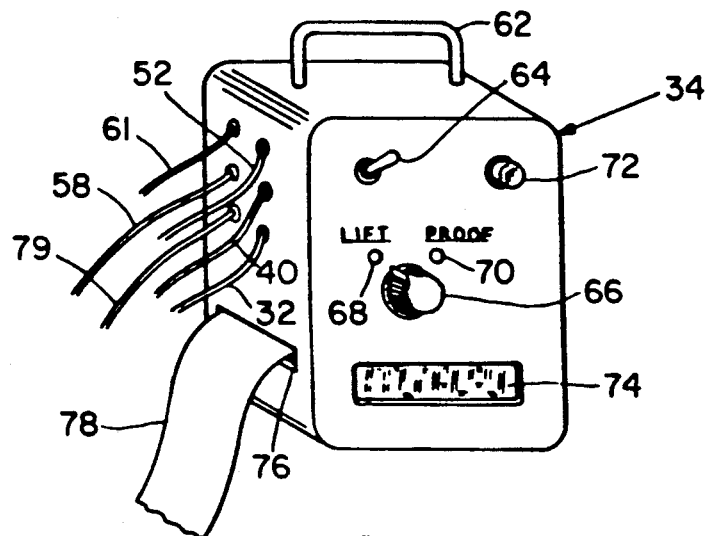
FIG. 4 is a perspective view of the control module employed in the system of FIG. 1.
Figure 5:
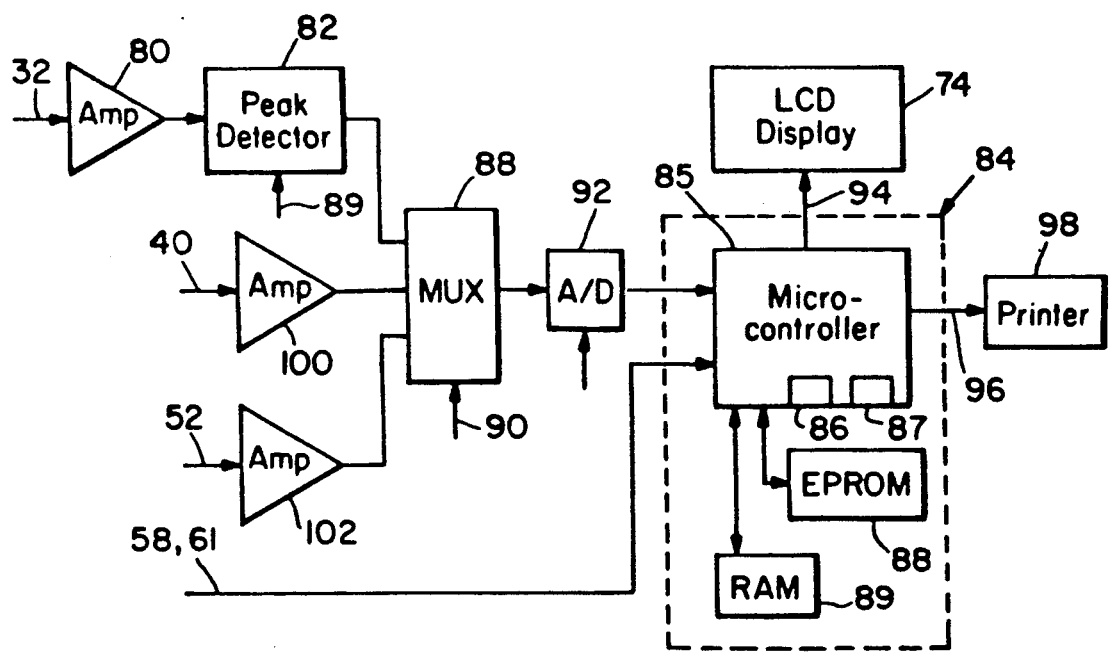
FIG. 5 is a block diagram of circuitry of the control module of FIG. 4.

The portable, battery-powered control module 34 is shown in FIG. 4, and a block diagram of its circuitry is shown in FIG. 5. That module includes carrying handle 62, on/off switch 64, mode selector switch 66 that has compaction mode position 68 and proof mode position 70; reset button 72; LCD display 74 and printer output 76 that produces a printed record 78 of compaction results.

With reference to FIG. 5, input lines 32 (from perimeter sensors 30A-D that are connected in parallel) are connected through adjustable gain amplifier 80 to peak detector 82 that has an input 83 from microprocessor 84. Microcontroller 85 includes accumulator 86 and timing counter 87; and coupled to microcontroller 85 are EPROM 88 and RAM 89. The output of peak detector 82 is applied through multiplex unit 88 that has an input 90 from mode selector switch 66 and analog to digital converter 92 to microcontroller 86 which provides an output over line 94 to LCD display 74 and over line 96 to printer 98. A second input to control module 34 is over lines 40 (from center sensor 38 through adjustable gain amplifier 100 to multiplexer 88); a third input over lines 52 from sensor 50 that is used with proofing hammer 60 and is applied through adjustable gain amplifier 102; and a fourth (trigger) input over line 58 from proofing plate 56 and line 61 from hammer 60. Peak detector 82 includes circuitry that accumulates peak values of signals on line 32 and averages those peak values for application through multiplexer 90 and analog to digital converter 92 for storage by accumulator 86 and display of the average value by display 74. Peak detector 82 is reset periodically (automatically by microcontroller 85) to provide a series of average impact values as sensed by sensors 30A-D. Processor 84 stores the magnitude of those averaged impact values (which increase as the backfill material is compacted and thus better transmits the impact energy to sensors 30) and compares the sensed impact values of preceding passes with those of the current pass and when they are substantially uniform (e.g., the average value of impact generated signals during the current pass being less than five percent greater than the average signal value during the immediately preceding pass), microprocessor 84 causes display 74 to provide an indication of satisfactory compaction of that lift.

Figure 6:
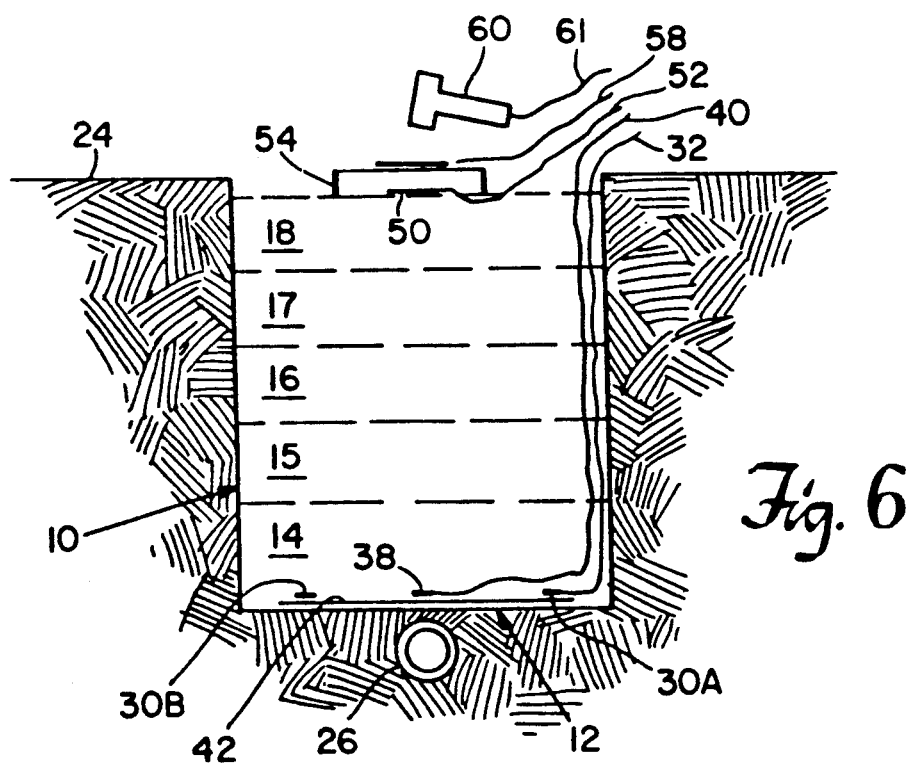
FIG. 6 is a sectional diagrammatic view of system operation in proofing mode.

In system use, with reference to FIG. 6, after gas line 26 at the base of utility excavation 10 has been covered with a thin layer of backfill material, sensor module 12 is placed at the bottom of excavation 10 with connecting conductors 32, 38 leading up out of the excavation to the control module 34. The distance from the central sensor 38 to the top of the hole 10 is measured and entered into control module 34, (for example, manually or with a sonic transmitter-receiver unit 75 that is supported directly above sensor 38 by rod 77 that is positioned on road surface 24 to bridge hole 10 and a depth measurement is made sonically and entered into processor 84). A lift 14 of backfill material is placed in the excavation and compacted with compaction tool 22 which may be manual or hydraulic as appropriate depending on the particular application. As the lift 14 is being compacted in a series of "passes", the compaction is monitored by control module 34 in compaction mode by sensing the amplitude of signals over lines 32 from the perimeter sensors 30. Each compacting blow from compacting tool 22 transmits seismic energy through the backfill lift 14 to the sensors 30 which produce output voltages proportional to the sensed impact energies. A hydraulic compacting tool typically generates several compacting blows a second, and during each pass, the peak amplitude of signals on lines 32 as indicated by peak detector 82 is read by control module 34 at one hundred millisecond intervals and transferred through multiplexer 90 and A-D converter 92 for storage in accumulator 86. Peak detector 82 is reset automatically by microcontroller 85 after each interval so that a series of average impact values are stored by accumulator 86. Those averaged impact values (which increase as the backfill material is compacted with corresponding improvements of the transmission of impact energy to sensors 30) of a preceding pass are compared with those of the current pass and when the average value of impact generated signals during the current pass is less than a predetermined amount (e.g., five percent) greater than the average impact signal values during the immediately preceding pass, microprocessor 84 causes display 74 to provide an indication of satisfactory compaction of lift 14. Lifts 15-18 are similarly backfilled and compacted.

After the several lifts 14-18 have been satisfactorily compacted in sequence, the distance between the top of the hole 10 (original surface 24) and the surface of lift 18 is measured and entered into control moldule 34 as an offset from the earlier entered excavation depth measurement. Proofing sensor 50 is placed on the center of the top of lift 18 of the backfill material (immediately above the center sensor 38), spacer 54 is placed on the surface of backfill lift 18 surrounding sensor 50 and is filled with backfill material 79 that is compacted as appropriate to provide a thickness of about five centimeters, and proofing plate 56 is placed on top of the backfilled spacer 54, as indicated in FIG. 6. Mode selector switch 66 is placed in proof mode position 70 and proofing plate 56 is then struck with hammer 60, generating an initializing signal over lines 58, 61 to microprocessor 84 to initialize the microprocessor circuitry that includes timer counter 87. Proofing sensor 50 in response to sonic energy from proofing plate 56 transmits an impulse over lines 52 and through multiplexer 90 to microprocessor 84 to start the timer counter 87. The sonic energy from the hammer 60 striking plate 56 is subsequently sensed by sensor 38 and supplied over lines 40 through amplifier 100 to microprocessor 84 to stop counter 87. The counter value (which represents propagation time between sensors 50 and 38) is then used to calculate velocity, on the basis of the known distance between sensors 38 and 50, as an indication of the quality of compacted backfill in excavation 10. The parameters of that compacted backfill quality can be inputed to microprocessor 84 in terms of characteristics of the backfill material and depth of the excavation (distance between sensors 38 and 50) or the time difference (propagation time) may be displayed directly as an indication of compaction quality in terms of characteristics of the backfill material and depth of the excavation 10 based on empirical data.

While a particular embodiment of the invention has been shown and described, various modifications will be apparent to those skilled in the art, and therefore it is not intended that the invention be limited to the disclosed embodiment or to details thereof, and departures may be made therefrom within the spirit and scope of the invention.

What is claimed is:

1. Apparatus for monitoring the compaction of backfill material in an excavation comprising
   hammer structure for impacting backfill material in the excavation,
   a sensor module for disposition at the bottom of the excavation to be backfilled that includes a transducer for developing an electric signal in response to energy transmitted through backfill material from said hammer structure, and
   a control module responsive to electric signals from said sensor module for providing an indication of the quality of compaction of backfill material in the excavation.

2. The apparatus of claim 1 wherein said sensor module includes a compliant base member of electrically-insulating material on which a plurality of said transducers are secured in spaced array.

3. The apparatus of claim 1 wherein said transducer is of the piezoelectric type.

4. The apparatus of claim 1 and further including another transducer for disposition at the top of the backfill material, and wherein said control module includes verifying circuitry responsive to a transducer on said sensor module and said another transducer for providing a transit time indication of impact energy propagation between said another transducer at the top of the backfill material and the transducer on said sensor module at the bottom of said excavation.

5. The apparatus of claim 1 wherein said control module includes timing circuitry for providing an indication of impact energy propagation time through backfill material to provide an indication of acceptable compaction of backfill.

6. The apparatus of claim 1 wherein said control module has a compaction mode for monitoring the progress of compaction of individual lifts and a proofing mode for providing an indication of acceptable compaction of backfill material in the excavation.

7. Apparatus for monitoring the compaction of backfill material in an excavation comprising
   hammer structure for impacting backfill material in the excavation,
   a sensor module for disposition at the bottom of the excavation to be backfilled that includes a transducer for developing an electric signal in response to energy transmitted through backfill material from said hammer structure, said sensor module including a compliant base member of electrically-insulating material, a plurality of first piezoelectric transducers secured in spaced array on said base member and connected in parallel to first output conductor structure, a second piezoelectric transducer secured on said base member and connected to second output conductor structure, and protective sheet structure overlying said transducers, and
   a control module responsive to electric signals from said sensor module for providing an indication of the quality of compaction of backfill material in the excavation,
   said output conductor structures being connected to said control module for transmitting electrical signals to said control module.

8. Apparatus for monitoring the compaction of backfill material in an excavation comprising
   hammer structure for impacting backfill material in the excavation,
   a sensor module for disposition at the bottom of the excavation to be backfilled that includes a transducer for developing an electric signal in response to energy transmitted through backfill material from said hammer structure, and
   a control module responsive to electric signals from said sensor module for providing an indication of the quality of compaction of backfill material in the excavation,
   said control module including accumulator circuitry for accumulating output signals from said sensor module for providing an indication of the quality of compaction of backfill material in the excavation.

9. Apparatus for monitoring the compaction of backfill material in an excavation comprising
   hammer structure for impacting backfill material in the excavation,
   a sensor module for disposition at the bottom of the excavation to be backfilled that includes an array of piezoelectric elements for developing an electric signal in response to energy transmitted through backfill material from said hammer structure, and
   a control module responsive to electric signals from said sensor module for providing an indication of the quality of compaction of backfill material in the excavation,
   said control module including peak detection circuitry for sampling electrical signals received from said array of piezoelectric elements, storage circuitry for storing indications of the peak of largest magnitude received during a sequence of compaction inpacts, circuitry responsive to said storage circuitry for providing average peak value signals during a pass of said hammer structure, and comparison circuitry for comparing the average peak value signals during a previous compaction pass with average peak value signals during the current composition pass to provide an indication of the progress of the compaction process.

10. Apparatus for monitoring the compaction of backfill material in an excavation comprising
hammer structure for impacting backfill material in the excavation,
a sensor module for disposition at the bottom of the excavation to be backfilled that includes a transducer for developing an electric signal in response to energy transmitted through backfill material from said hammer structure,
said sensor module including a compliant base member of electrically-insulating material, PVDF transducer structure secured on said base member and connected to output conductor structure, and protective sheet structure overlying said transducer structure,
another transducer for disposition at the top of the backfill material, and
a control module responsive to electric signals from said sensor module for providing an indication of the quality of compaction of backfill material in the excavation, said output conductor structure being adapted to be connected to said control module for transmitting electrical signals from said transducer structure to said control module.
said control module including verifying circuitry responsive to transducer structure on said sensor module and said another transducer for providing a transit time indication of impact energy propagation between said another transducer at the top of the backfill material and said transducer structure on said sensor module at the bottom of said excavation.

11. The apparatus of claim 10 and further including a plurality of PVDF transducer secured in spaced array along the perimeter of said base member and adapted to be connected by second output conductor structure to said control module.

12. The apparatus of claim 11 wherein said control module includes peak detection circuitry for sampling electrical signals received from said array of PVDF transducers, storage circuitry for storing indications of the peak of largest magnitude received during a sequence of compaction impacts, circuitry responsive to said storage circuitry for providing average peak value signals during a pass of said hammer structure, and comparison circuitry for comparing the average peak value signals during a previous compaction pass with average peak value signals during the current compaction pass to provide an indication of the progress of the compaction process.

13. A method for monitoring the compaction of backfill in an excavation comprising steps of
placing sensor structure at the bottom of said excavation,
adding backfill material to said excavation,
compacting said backfill material with a series of compacting impacts, and
monitoring the output of said sensor as a function of energy from said impacts that impinge on said sensor structure.

14. The method of claim 13 and further including the step of measuring the propagation time of an energy wave induced by the impacts from the top of said backfill material to said sensor structure to provide an indication of the quality of the compaction of the backfill material.

15. The method of claim 13 wherein said sensor structure includes a compliant base member of electrically-insulating material on which a plurality of piezoelectric transducers are secured in spaced array, and said base member has an area at least about one-half the base area of said excavation.

16. A method for monitoring the compaction of backfill in an excavation comprising steps of
placing sensor structure at the bottom of said excavation,
adding backfill material to said excavation,
compacting said backfill material with a series of compacting impacts, and
monitoring the output of said sensor as a function of energy from said impacts that impinge on said sensor structure, including the step of accumulating a plurality of impact signals from said sensor during a compaction pass to provide an indication of the progress of the compaction process.

17. A method for monitoring the compaction of backfill in an excavation comprising steps of
placing sensor structure at the bottom of said excavation, said sensor structure including a compliant base member of electrically-insulating material on which a plurality of piezoelectric transducers are secured in spaced array, and said base member having an area at least about one-half the base area of said excavation,
adding backfill material to said excavation,
compacting said backfill material with a series of compacting impacts, and
monitoring the output of said sensor as a function of energy from said impacts that impinge on said sensor structure, including a compaction mode step that includes accumulation of a plurality of impact signals from said transducers during a compaction pass to provide an indication of the progress of the compaction process, and a proofing mode step that includes measuring the propagation time of an energy wave from the top of backfill material in said excavation to a piezoelectric transducer on said base member to provide an indication of the quality of the compaction of the backfill material in said excavation.

* * * * *